United States Patent [19]

Narayanan et al.

[11] Patent Number: 5,071,463

[45] Date of Patent: Dec. 10, 1991

[54] DELIVERY SYSTEM FOR AGRICULTURAL CHEMICALS

[75] Inventors: Kolazi S. Narayanan, Palisades Park; Ratan K. Chaudhuri, Butler; Manilal Dahanayake, Wayne, all of N.J.

[73] Assignee: ISP Investments Inc., Wilmington, Del.

[21] Appl. No.: 448,707

[22] Filed: Dec. 11, 1989

[51] Int. Cl.$^5$ .................................. A01N 25/00
[52] U.S. Cl. ................................. 71/79; 514/788
[58] Field of Search ............ 514/408, 424, 936, 946, 514/947, 788; 71/DIG. 1, 93

[56] References Cited

U.S. PATENT DOCUMENTS 4,086,356 4/1978 Schneider et al. ............... 514/424
4,840,663 6/1989 Quadranti et al. ................. 71/93

FOREIGN PATENT DOCUMENTS 2128225 12/1972 Fed. Rep. of Germany.

OTHER PUBLICATIONS

Chemical Abstracts (75:109261k) 1971.
Chemical Abstracts (78:80918d) 1973.
Chemical Abstracts (111:111041u) 1989.

Primary Examiner—Frederick E. Waddell
Assistant Examiner—Kevin Weddington
Attorney, Agent, or Firm—McAulay Fisher Nissen Goldberg & Kiel

[57] ABSTRACT

An emulsifiable concentrate comprising an agriculturally active chemical, a surfactant, an organic diluent and a solvent having first and second components, the first component being capable of solubilizing the agriculturally active chemical and the second component in conjunction with the surfactant being effective to disperse the agriculturally active chemical. The inventive concentrate allows for high concentrations of the active ingredient, exhibits excellent stability and produces highly stable compositions upon dilution with water.

2 Claims, No Drawings

DELIVERY SYSTEM FOR AGRICULTURAL CHEMICALS

BACKGROUND OF THE INVENTION

I. Field of the Invention

The invention relates to a delivery system for agriculturally active chemicals. More particularly, the invention relates to an emulsifiable concentrate of difficult to dissolve agricultural chemicals.

II. Descriotion of the Prior Art

Agricultural chemicals are most preferably applied in the form of aqueous emulsions, solutions, or suspensions. Occasionally, they may also be applied in the form of a dust wherein the active ingredient is adsorbed onto or mixed with a finely divided inert carrier material, such as, china clay, or the like. With such powdered or dust compositions, drift due to wind is a problem and consequently, liquid formulations are preferred.

One of the problems with such liquid formulations is the fact that chemicals having agricultural activity often exhibit extreme insolubility in water. This results in their having to be dissolved either in organic solvents or utilized in the form of emulsions or suspensions. With respect to the use of organic solvents, these are generally disadvantageous from an environmental and cost view point. Particularly, such organic chemicals may exhibit toxicity or side-effects which may be adverse to the effect of the agricultural chemical itself or to the subsequent fruit or vegetable produced in the particular agricultural use. This toxicity may also be disadvantageous with respect to handling.

When attempts are made to provide emulsified or suspension formulations, difficulties are encountered with respect to providing a desirably high concentration of the agriculturally active ingredient. Thus, when such agriculturally active chemicals are formulated into an emulsion, it is difficult to maintain the emulsified state. This makes it difficult to maintain a uniform formulation, particularly, when the formulation is diluted with water for application to the plants.

Typically, for example, the agriculturally active ingredient is mixed with one or more of a variety of conventional solvents and an emulsifying agent to form a concentrate. This concentrate may be an emulsion, suspension, or solution. The concentrate is then stored until it is transported to the site of use or may simply be transported and stored at the site of use. In any event, the concentrate normally will undergo some poeriod of storage until it is ready for use. Undertandably, it is most desirable to be able to transport the argiculturally active ingredient at the highest concentration possible so as to minimize the volume of material which need be transported. By the same token, however, at the use site, it is normally not feasible to admix ingredients together or to process them other than to·dilute the concentrate with water. Accordingly, it is important that the concentrate emulsify easily, i.e., exhibit good "bloom", upon the addition of water. In addition, at the use site, it is often necessary to store the diluted concentrate for extended time periods until the actual application to the plants. Consequently, it is important that the diluted form of the concentrate exhibit good stability with respect to the uniformity of the emulsion and to avoid precipitation of the active ingredients. If non-uniformity or precipitation occurs in the diluted form, then non-uniformity will result in the application of the diluted formulation to the plants.

An attempt to provide concentrates of agriculturally useful chemicals is disclosed in South African Patent application No. 695,393, filed July 25, 1969. This application is directed to the formulation of a concentrate substantially water-insoluble pesticides for agricultural use. The peticides, either in oil or solid form, are mixed with pyrrolidones having a hydrogen or a lower alkyl group containing from 1 to 4 carbon atoms attached to the nitrogen atom of the pyrrolidne ring. The application discloses that concentratied solutions of difficult to dissolve perticides could be formulated and that such concentrates exhbiited good stability. The concentrates utilized are those containing the pesticidal active ingredient, the particular lower alkyl pyrrolidone, a co-solvent which is usually a common organic solvent, such as, an aromatic including xylene, methylated and polyalkylated naphthalenes and aliphatic solvents, and a dispersing or emulsifying agent, such as, a surfactant, including polyoxyethylene alkylphenols, polyoxyethylene fatty esters, polyoxyethylene sorbitan fatty esters which may be blended with oil-soluble sulfonates, calcium and amino-sulfonate salts, and the like.

This prior art does not offer a solution to the problem arising from the difficulty in maintaining the stability of the emulsion after the concentrate is diluted with water. Consequently, unless the diluted form of the concentrate is used immediately after emulsification, it is difficult to provide a stable diluted formulation for application to the plants.

U.S. Pat.No. 4,798,837 discoloses an emulsifiable concentrate of the pesticidal compound (CGA):

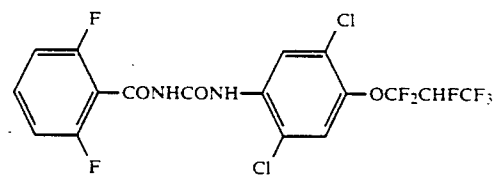

This active concentrate contains 10% of the active ingredient using 30% cyclohexanone as the solvent. However, cyclohexanone is highly toxic. For such agricultural uses, it is desirable to avoid the use of toxic solvents, including those of Lists 1 and 2 of 40 C.F.R. 154.7 dated Apr. 22, 1987, which includes inerts of toxicological concern and solvents having high flash points, as well as to increase the amount of the agriculturally active material in the concentrate.

SUMMARY OF THE INVENTION

We have discovered a novel emulsifiable concentrate of an agriculturally active chemical, which concentrate provides, upon dilution, a highly stable emulsion. In addition, the inventive emulsifiable concentrates may contain relatively high concentrations of th agriculturally activé ingredient making it advantageous from both economic and handling viewpoints. Also, the concentrates of the present invention utilize organic materials which do not pose environmental problems either in use or handling.

More particularly, the emulsifiable concentrate of the present invention is composed of an agriculturally active chemical, a surfactant, an organic diluent, and a solvent having a first component and a second component.

The first component of the solvent is selected from those compounds which have a sufficiently high hydrophilic property to solubilize the agriculturally active chemical. Preferably, the first component will have the following Hansens' solvent parameters:

Dispersable component from about 40 to 50%; Polar components of from about 25 to 40%; and H-bonding components of 10 to 30%.

The second component is a hydrophobic solvent having the following Hansens+ solubility parameters:

Dispersive component from about 56 to 75%; Polar component from about 8 to 24%; and H-bonding component of from about 10 to 30%.

This second component should also have surfactant properties and act as a non-ionic surfactant with an HLB value ranging from about to 2 to 8.

For a discussion of the solubility parameters, see *C.R.C. Handbook of Solubility Parameters and Other Cohesion Parameters*, Allan F.M. Barton, 1983, Table 9, p. 167-170.

DESCRIPTION OF THE PREFERRED EMBODIMENT

As used herein, the term "agriculturally active chemical" includes compounds and mixtures thereof which can be used as agricultural fertilizers, nutrients, plant growth accelerants, herbicides, plant growth controlling chemicals, and chemicals which are effective in killing plants, insects, microorganisms, fungi, bacteria and the like which are commonly referred to as insecticides, bactericides, fungicides, nematocides, fumigants, and the like, as well as any other chemicals having properties which are suitable for agricultural uses in terms of application to plants or domestic uses for controlling insects and pests. Particularly, such chemicals would normally take the form of water-immiscible or oily liquids and/or solids which is substantially insoluble in water. By the term "substantially insoluble", it is meant that for all practical purposes, the solubility of the compound in water is insufficient to make the compound practicably usable in an agricultural end use without some modification either to increase its solubility or dispersability in water, so as to increase the compound's bioavailability or avoid the use of excessively large volumes of solvent.

Suitable agriculturally active chemicals which can be used with the present invention include insecticides, such as, cyclocompounds, carbamates, animal and plant derivatives, synthetic pyrethroids, diphenyl compounds, non-phosphates, organic phosphates, thiophosphates, and dithiophosphates. (See *Argicultural Chemicals*, Book I, *Insecticides*, 1989 Revision by W. T. Thomson, Thomson Publications.) Typical of the insecticides are:

cyclocompounds:
  6,7,8,9,10,10,-hexachloro-1,5,5a,6,9,9a-hexahydro-6,9-methano-2,4,3-benzodioxathiepin-3-oxide
carbamates:
  2-isopropyl phenyl-N-methyl carbamate;
  2-(1,3-dioxolan-2-yl) phenylmethyl carbamate; 2,3-isopropylidine dioxyphenyl methyl carbamate;
animal and plant derivatives:
  chlorinated hydrocarbons derived from Southern pine; naturally occuring lactone glycoside;
synthetic pyrethroids:
  (±) α-cyano-3-phenoxybenzyl (±) dis, trans 3-(2-2-dichlorovinyl)-2,2-di-methyl cyclopropane carboxylate;
  (±) cyano (3-phenoxyphenyl methyl (±)-4-(difluoromethyoxy) α-(1-methylethyl) benzene acetate;
phenoxy compounds and non-phosphate:
  2,2-bis (p-methoxy phenyl)-1,1,1,tri-chloroethane;
  1,3,5tri-n-propyl-1,3,5-triazine-2,4,6 (1H, 3H, 5H) trione; ethyl (2E, 4E)-3,7,11-trimethyl-2,4-dodeca dienoate;
  1-decycloxy 4-[(7-oxa-oct-4-ynyl)]-oxybenzene;
organic phosphates:
  dimethyl phophate ester of 3-hydroxy-N,N-dimethyl-cis-crotonamide; 2-chloro-1-(2,4-dichloro phenyl) vinyl diethylphosphate;
  4-(methyl thio) phenyl dipropyl phosphate;
thiophosphates:
  0,0-diethyl-0-4-nitrophenyl phosphorothioate;
  0,0-diethyl-0-(2-isopropyl-6-methyl-5-pyrimidinyl) phosphorothioate;
  2-diethylamino-6-methyl pyrimidine-4-yl dimethyl phosphorthioate;
dithiophosphates:
  0,0-dimethyl phosphorodithioate ester of diethylmercapto succinate;
  0-ethyl-S-phenyl ethyl phosphorodithioate.

Typical herbicides include phenoxy compounds, benzoic, acetic, and phthalic acids, aniline derivaties, niriles, amides, acetamides, anilides, carbamates, thiocarbamates, and heterocyclic nitrogen derivatives, e.g., triazines, pyridines, pyridazones, picolinic acid, and urea derivates and phosphates. (See *Aoricultural Chemicals*. Book II, *Herbicides*, 1986-87 Edition, W. T. Thomson, Thomson Publications, Fresno, CA 93791.) Exemplary of the above compounds are:

phenoxy compounds:
  2,4-Dichlorophenoxy acetic acid 2,4,5-trichloro phenoxyacetic acid; 4-(2,4-dichlorophenoxy) butyric aicd;
  S-ethyl 2 methyl-4-chlorophenoxy-thioacetate;
  2-methyl-4-chloro-phenoxy acetic acid;
  methyl 5-(2,4-dichloro-phenoxy)-2-nitrobenzoate;
benzoic and acetic acids of phthalic compounds:
  3,6-dichloro-o-anisic acid
  4-chloro-2-oxo benzothiazolin-3-yl acetic acid;
  N-1-Naphthyl-pthalamic acid;
nitriles and aniline derivatives:
  3-5-dibromo-4-hydroxybenzo-nitrile; α,α,α,-trifluoro-2,6-dinitro-N, N-dipropyl-p-tolinidine;
  N-(1-ethylpropyl)-2,6-dinitro-3,4-xylidine;
amides, acetamides, anilides:
  N,N-diethyl-2-(1-naphthalenyl oxy)-propionamide;
  2,6-dimethyl-N-2'methoxy-ethyl-chloro-acetanilide;
  3',4'-dichloro-propionanilide;
  α-chloracetic-N-(3,5,5-trimethyl-cyclohexen-1-yl)-N-isopropylamide;
  4-benzyl-N-isopropyl trimethyl acetamide;
thiocarbamates:
  S-Ethyl dipropyl thiocarbamate;
urea derivatives:
  3-(5-tert-butyl-3-isoxazoyl)-1,1dimethyl urea;
  N-(2,6-trifluoro-benzoyl)-N'-[2,5-dichloro-4-(1,1,2,3,3,3-hexafluoro-propyloxy) phenyl]urea;
pyrrolidone derivatives:
  1-(m-trifluoro methyl phenyl)-3-chloro-4-chloromethyl-2-pyrrolidone;
amino acid derivatives:

methyl-N-benzoyl-N-(3-chloro-4 fluorophenyl)-DL alarinate; N-chloroacetyl-N-(2,6-diethyl phenyl)-glycine ethyl ester;

carbamates:
  Isopropyl-m-chlorocarbanilate; 3-Ethoxy (carbonyl aminophenyl)-N-phenyl carbamate;

heterocyclics:
  4-amino-3,5-dichloro-6-fluoro-2-pyridyloxy acetic acid;
  4-(1,2-Dimethyl-N-propyl amino)-2-ethyl amino-6-methyl thio-S-riazine;
  2-[4,5-dihydro 4-methyl-4-(1-methyl ethyl)-5-oxo-1 H-imidazoyl-2yl-3-byridinecarboxylic acid;
  2-[3,5-dichlorophenyl)-2-2,2,2-trichloroethyl) oxiane; Butyl-9-hydro-fluoroene-(9)-carboxylate;
  2-[1-(ethoxy imino) butyl]-3-hydroxy-5-(2H-tetra hydro thiopyran-3)-2-cyclohexene-ione;
  2-(2 chlorophenyl) methyl-4,4-dimethyl-3-iso oxazolidinone;

phosphates:
  0-ethyl-0-(3-methyl-6-nitro phenyl) N-sec-butyl phosphoro thio amidate.

Typical fungicides include (See *Agricultural Chemicals*, Book IV, *Fungicides*, 1989 Revision, W. T. Thomson, Thomson Publications, Fresno, CA 93791):

organic compounds:
  2,5-dimethyl-N-Cyclohexyl-N-methoxy-3-furan carboxamide;
  5-Ethyoxy-3-trichloromethyl-1,2,4-thiadiazole;
  3-(2-methyl piperidino) propyl dichlorobenzoate;
  N,N'-(1,4-piperazinediyl bis (2,2,2-trichloro) ethylidene) bis formamide;
  Tetramethyl thiuram disulfide; 0-Ethyl-S,S,diphenyl-dithiophos-phate;
  5,10-dihydro-5,10-dioxo naptho (2,3,9)-p-dithiin-2,3-dicarbo-nitrile;
  2-(thiocyano methyl thio) benzothia-zole;
  α-2-(4-chlorophenyl) ethyl]-α-(1,1-dimethyl ethyl)-1 H-1,2,4-triazole-1-ethanol;

morpholines:
  N-tridecyl-2,6-dimethyl morpholine;
  4-N-dodecyl-2,6-dimethyl moropholine;

Typical fumigants, growth regulators, repellants, and rodenticides include (See *Agricultural Chemicals*, Book III, 1988-1989 Revision, W. T. Thomson, Thomson Publications, Fresno, CA 93791):

growth regulants: 1,2 Dihydro-6-ethoxy-2,2,4-trimethylquinoline;
  (2-chloroethyl) phosphoric acid; 4-[acetamino) methyl]-2-chloro-N (2,6-diethyl phenyl acetamide;
  Benzoic acid, 3,6 dichloro-2- methoxy,2-ethoxy-1-methyl-2-oxo ethyl ester;

repellants:
  0,0-dimethyl-0-[(4-m-tolyl] phosphorothioate;
  Tetriary butyl-sulfenyl dimethyl dithio carbamate;

seed softener:
  2-chloro-6-(trichlomethyl) pyridine; 5-ethoxy-3-trichloromethyl-1,2,4-thiadiazole;
  N-phenyl-N'-1,2,3-thiadiazol-5-yl urea;

Pesticides may be characterized by their physical properties depending on their physical state at normal or ambient conditions, i.e., between 40° F. and 90° F. and their solubility or miscibility with water or other common organic solvents, e.g., aromatics, such as, toluene, xylene, methylated and polyalkylated naphthalenes, and aliphatic solvents.

Based on the physical properties, the pesticides may be classified into two groups. The first group includes those which are oily liquids at ambient temperatures and are immiscible with water. Specific pesticides include:

Common esters of 2,4-dichlorophenoxyacetic acid,
Common esters of 2,4,5-trichloro-phenoxyacetic acid,
Common esters of 2-(2,4-dichlorophenoxy) propionic acid,
Common esters of 2-(2,4,5-trichlorophenozy) propionic acid,
Common esters of 2,4-dichlorobutyric acid,
Common esters of 2,methoxy-3,6-dichlorobenzoic acid,
Common esters of 2-methyl-4-chlorophenoxyacetic acid,
Piperonyl butoxide 3,4-methylenedioxy-6-propyl benzyl n-butyl diethylene glycol ether,
Bromophos ethyl: 0,0-diethyl-0-2,5-dichloro-4-bromophenyl thionophosphate,
N-(2-mercaptoethyl) benzene-sulfenamide (BETASAN®),
Isobornyl Thiocyanoacetate (Thanite®),
Ioxynil ester of octanoic acid,
Molinate S-ethyl hexahydro - 1 H - azepine-1-carbothioate,
PP 5111 0,0-dimethyl-(2-diethylamine 4-methyl-6-pyrimidinyl) carbamate,
PP 211 0,0-diethyl 0-(2-diethylamine-4-methyl-6-pyrimidinyl) phosphorocarbamate,
Chlordane
5-Ethoxy-3-(trichlorometyl)-1,2,4-thiadiazole (TERRAZALE®), Ethyl-s-s-dipropyl-phosphodithioate (MOCAP®),
S-Ethyl dipropylthiocarbamate (EPTAM®),
S-Ethyl diisobutylthiocarbamate (SUTAN®),
S-n. propyl-di-n-propylthiocarbamate (VERNAM®),
S-propyl butylethylthiocarbamatae (TILLAM®),
S-ethyl ethylcyclohexylthiocarbamat (RO-NEET®),
Malathion (S-(1,2-dicarboxyethyl)-0,0-dimethyl phosphorodi-thioate),
Diazinon (0,0-diethyl,0-(2-isopropyl-4-methyl-6-pyrimidinyl) phosphorothioate,
0-Ethyl-S-phenyl-ethylphosphonodithioate Toxaphene (Octachlorocamphene),
Bromoxynil (3,5-dibromo-4-hydroxy benzonitrile ester of n.octanoic acid,
2-chloro-N-2,6-diethylphenyl-N-methoxymethylacetamide (LASSO®),
Diallate S-2,3-dichloroallyl N,N-diisopropylthiolcarbamate,
Triallate S-2,33-trichloroallyl N,N-diisopropylthiolcarbamate.

The second group comprises those pesticides which are solids at ambient temperatures and for all practical purposes, insoluble in water.

2,4,5-T (2,4,5-trichlorophenoxy acetic acid)
1,1-dimethyl urea)
Monuron (3-(p-chlorophenyl)--1,1-dimethyl urea)
Diuron (3-(3,4-dichlorophenyl)-1,1-dimethyl urea)
Bromacil (5 bromo-3-sec. butyl-6-methyl uracil)
Isocil (5 bromo-3-isopropyl-6-methyl uracil)
Linuron (3-(3,4 dichlorophenyl)-1-methoxy-1 methyl urea
Atrazine (2-chloro-4-ethylamino-6 isopropylamino-s-trriazine)
Simazine (2-chloro-4,6,-bis (ethylamino)-s-triazine
Dodine (n-dodecylguanidine acetate)
Thiram (tetramethylthiuram disulfide)

N-(mercaptomethyl)phthalimide s-(o,o dimethylphosphoro-dithioate) (IMIDAN ®)
Lindane (gamma 1,2,3,4,5,6 hexachlorocyclohexane)
Folpet (N-trichloromethylphthalimide)
Manazon (s-(4,6-diamino-1,3,5-triazin-2-yl methyl)-dimethyl phosphorothiolthionate)
Barban (4-chloro-2 butynyl m-chlorocarbanilate)
Tricumba 2-methoxy-3,5,6-trichlorobenzoic acid
Trifluralin (2,6-dinitro-N,N-dipropyl-4-trifluoro-methylamiline) (2,3 dihydro-5-carboxanilido-6-methyl-l,4-oxathiin) (VITAVAX ®)
2,4-dichlorophenoxyacetic acid
4-(4-chloro-2 methylphenoxy) butyric acid
2-(2,4-dichlorophenoxy) propionic acid
Ioxynil: 3,5 diiodo-4-hydroxybenzonitrile Bromoxynil: 3,5 dibromo-4-hydroxybenzonitirle
Carbaryl: 1-naphthyl-N-methylcarbamate
Methoxychlor: 2,2,-Bis(p-methoxyphenyl)-1,1-trichloroethane
PP 781: 4(2-chloro phenylhydrazono)-3-methyl-5-isoxazolone*
PP 675: 5-butyl-2-dimethylamino-4-hydroxy-6-methyl pyrimidine* dimethylcarbamate*
Manufactured by Imperial Chemical Industries Limited
PP 149: 5-n-butyl-2 ethylamino-4-hydroxy-6 methyl-pyrimidine*
C 6313 N'-(4-bromo-3-chlorophenyl)-N-methoxy-N-methylurea
C 6989 2,4'dinitro-4-trifluoromethyl-diphenylether
Chloroxuron N'-4-(chlorophenoxy) phenyl-NN-dimethylurea
Dichlobenil 2,6-dichlorobenzonitrile
Diphenamid NN-dimethyl-2,2-diphenylacetamide
Fenac 2,3,6-trichlorophenylacetic acid
Fluometuron N'-(3-trifluoromethylphenyl)-NN-dimethylurea
GS 14260 4-ethylamino-2-methylthio-6-t-butyl-amino-1,3,5-triazine
PCP Pentachlorophenol
Lenacil 3-cyclohexyl-6,7-dihydro-lH-cyclo-pentapyrimidine-2,4-(3H,5H)-dione
Pyrazon 5-amino-4-chloro-2-phenyl-3-pyridazone
Metrobromuron N'-(4-bromophenyl)-N-methoxy-N-methylurea
Metoxymarc N-(4-methoxybenzoyl)-N-(3,4-dichlorophenyl)-N',N'-dimethylurea
Neburon N-butyl-N'-(3,4-dichlorophenyl-N-methylurea
NIA 11092 1,1-dimethyl-3-[3-(n-t-butyl carbamyloxy)-phenyl]urea
Mecoprop 2-(4-chloro-2 methylphenoxy)propionic acid
Nitrofen 2,4-dichlorphenyl 4-nitrophenylether
Propanil N-(3,4-dichlororphenyl)propionamide
Pyriclor 2,3,5-trichloro-4-pyridinol
Solan 3'-chloro-2-methyl-p-volerotoluidide
Terbacil 5-chloro-3-t-butyl-6-methyluracil
UC 22463 (SIRMATE)-3,4-dichlorobenzyl N-methyl-carbamate
WL 9385 2-Azido-4-ethylamino-6-t-butylamino-s-triazine
Propachlor 2-chloro-N-isopropylacetanilide
CP 50144 2-chloro-N-2,6-diethylphenyl-N-methoxymethylacetamide
CP 31675 2-chloro-N-(2 methyl-6-t-butylphenyl)acetamide Cypromid 3',4'-dichlorocyclopropane carboxanilide
Fenuron NN-dimethyl-N'phenylurea
Chlorbromuron N'-(4-bromo-3-chlorophenyl)-N-methoxy-N-methyl-urea
Ametryen 2-methylmercapto-4-ethylamino-6-isopropyl-amino-s-triazine
Prometryne 2-methylmercapto-4,6-bisisopropyl amino
DCPA dimethyl 2,3,5,6, tetrachloroterephthalate
Benefin N-butyl-N-ethyl-2,2,2-trifluoro-2,6-dinitro-p-toluidine
Nitralin 2,6-dinitro-4-methylsulfonyl-NN-dipropyl-aniline
PP 493 2,6-difluoro-3,5-dichloro-4-hydroxy pyridine
CNP 2,4,6-trichlorophenyl-4'-nitrophenyl ether
Pentachloro nitrobenzine
1-(butile carbamoy)-2-benzimidazol carbamic acid, methyl ester (BENLATE ®)

Typical examples of first components suitable for use in the solvent are alkylpyrrolidones having from 1 to 4 carbon atoms in the alkyl group, cyclic lactones, e.g., gamma-butyrolactone, lower alkyl cyclic carbonates, i.e., ethylene carbonate, propylene carbonate, butylene carbonate, lower akylimidazolone, e.g., N-N,dimethylimidazolone, lower alkylamides of formic acid and acetic acid, e.g., dimethyl formamide and dimethylacetamide, and lower alkyl sulfoxides, e.g., dimethylsulfoxide. (The term "lower alkyl" in these examples means one or two carbons.) Mixtures of these may also be used as the first component.

Examples of appropriate second components include alkylpyrrolidones having an alkyl portion containing from 6 to 14 carbon atoms, e.g., octylpyrrolodone, dodecylpyrroli-done, or N-(2'-ethylhexylpyrrolidone), alkyl gamma-butyrolac-tones, alkyl cyclic carbonates and combinations thereof, wherein the alkyl chains contain from 6 to 14 carbon atoms. The alkyl portion may be distributed at one or more sites on the ring so long as one portion contains at least 6 carbon atoms and the total number of alkyl carbon atoms does not exceed 14. For each of the above examples, the 6 to 14 carbon alkyl portions may be straight or branched.

Preferably, the first component is selected from the group consisting of pyrrolidones having the formula

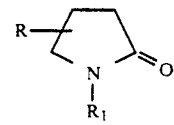

wherein R is hydrogen or lower alkyl having from 1 to 4 carbon atoms and R is lower alkyl having from 1 to 4 carbon atoms.

The second component is preferably selected from pyrrolidones having the formula

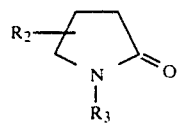

wherein $R_2$ is hydrogen or alkyl having from 6 to 14 carbon atoms and $R_3$ is alkyl having from 6 to 14 carbon atoms with the proviso that at least one of $R_2$ or $R_3$ must contain at least 6 carbon atoms and the sum of the carbon atoms in $R_2$ and $R_3$ cannot exceed 14.

The inventive composition further comprises an organic diluent which is a synthetic or naturally occurring oils having a high hydrophobic character or having a fractional dispersive solubility parameter of greater than 70% and preferably greater than 85% and a molar volume of greater than 90 cm³/mole. These properties are defined in the C. R. C. Handbook referred to hereinabove. Typical diluents include soybean oil, rapeseed oil, long chain alcohols, long chain ketones, long chain esters, and ethers. As used herein, "long chain" means with 6 or more carbon atoms. Also suitable as the organic diluent are aromatic petroleum oils including those which are commercially available distillates from crude oils having an average boiling point greater than 200° C. Typical of such materials are those sold under the trademarks Exxon 200 or Texaco 400. Of course, such aroma-tics should be approved for use as a carrier for agriculturally active chemicals.

The composition of the aromatic petroleum oil is generally:
Heavy aromatic solvent naphtha—about 60%;
Middle distillate solvent extractant—about 40%.

Normally, these oils contain predominantly the $C_9$–$C_{15}$ aromatic hydrocarbons and primarily the $C_{10}$–$C_{12}$ hydrocarbons having a flash point of about 203° F.

In the inventive composition, the amount of solvent is in the range from about 20 to 90%, and the amount of diluent is about 80 to 10%, based on the weight of solvent and diluent in the composition. With respect to the solvent, the amount of the first component is from about 5 to 95% and preferably, 20 to 80%; and the amount of the second component is from about 5 to 95%, and preferably, 20 to 80%, based on the weight of the solvent.

The inventive composition also contains one or more additional emulsifier or surfactant which is generally selected on a case by case basis in order to optimize the solubility and stability of the emulsion. Typically, such emulsifiers include ethoxylated alkyl phenols, linear aliphatic polyesters, linear aromatic polyesters, polyethoxylated alcohols, linear aliphatic ethoxylates, polyethoxylated castor oil, polyethoxylated carboxylates, and polyethoxylated alkylamines. Anionic surfactants may be used as the emulsifier and include phosphate esters and their salts, alkyl sulfonamides, salts of sulfated nonylphenoxypoly(ethyleneoxy) ethanol, salts of alkylbenzene sulfonates, salts of alkylnaphthalene sulfonate, and sulfonated aliphatic polyesters and their salts. Also suitable are complex phosphate esters of nonionic surfactants of the ethylene oxide type which are mixtures of diesters of phosphoric acid. (See, for example, McCutcheon's, Emulsifiers and Deteroents (1989), published by McCutcheon's Division of M.C. Publishing Co., Glen Rock, New Jersey.) Generally, the amount of emulsifier (surfactant) is from about 1 to 25% based on the total weight of the composition.

The agriculturally active chemical (sometimes referred to herein as AAC) concentration should be as high as possible so long as it does not precipitate out upon dilution of the concentrate with water for a reasonable period of time and achieves the desired effect. With the present invention, it is possible to obtain concentrates with agriculturally active chemical concentrations in excess of 5 weight percent which form a stable emulsion upon being diluted with water. Depending on the particular agriculturally active chemical, the concentration of the AAC is from about 5 to 60% based on the total weight of the composition before dilution.

The following examples illustrate the present invention*: * In the examples, all compositional percentages are percent by weight of the total composition unless otherwise indicated.

EXAMPLE 1

A series of twelve compositions wherein the amount of a first pyrrolidone component (N-methylpyrrolidone), second pyrrolidone component (N-octylpyrrolidone) and aromatic solvent were varied using a surface-active agent from 14.3% to 22.2% by weight and agriculturally active chemical from 25.8% to 41.6% by weight. (See Table 1.) The surface-active agent was Gafac RE-610 (ethoxylated phosphate ester), and the agriculturally active chemical (AAC) was N-(1-ethylpropy)-2,6-dinitro-3,4-xylidine (PRL).

Formulations:

Formulations were made by mixing together the components comprising of each composition by weighing the exact proportion of ingredients in a bottle. The solvents were weighed in first. The AAC was dissolved completely in the solvent system followed by addition of the wetting agent or emulsifying agent. Typically, about 20g of each of the formulations was prepared. As an illustration, formulation #11 included in Table 1-2 was prepared by weighing together the following ingredients in a one ounce bottle:

TABLE 1-1

| | | |
|---|---|---|
| N-methylpyrrolidone | 2.75 g | 20.4% |
| N-octylpyrrolidone | 1.25 g | 9.3% |
| Aromatic Petroleum oil Exxon 200 | 1.00 g | 7.4% |
| PRL (N-1 ethyl propyl)-2,6-dinitro-3,4-xylidine (92% Tech.) | 5.50 g | 40.7% |
| Phosphate ester (Gafac RE-610) | 3.00 g | 22.2% |
| TOTAL: | 13.50 g | 100.0% |

The contents were stirred well in an automatic rocking shaker for about 30 minutes when the AAC dissolved completely. The samples thus prepared were evaluated for freeze-thaw stability on storage and ease of emulsification and emulsion stability on dilution.

Freeze-Thaw Stability:

The concentrates were stored for a period of 24 hours in the cold temperature 5° C.) in a refrigerator and taken out and thawed to room temperature and then stored at 55° C. in an oven for a period of 24 hours. The alternate storage in the cold (5° C.) and warm condition at 55° C. was repeated for three cycles. Any separation during the storage was recorded. A concentrate is "stable" if there is no substantial separation after the 24 hour cycles at each temperature.

Evaluation of Emulsion Stability and Ease of Emulsification:

A Nessler tube (1.8 cm diameter; 28 cm long) was filled with appropriate quantity (47-48 g) of World Health Organization (WHO) standard (6g of $CaCl_2$ and 2.87 g of $MgCl_2 6H_2O$ dissolved in 20L) hard water having a hardness of 342 ppm expressed as Na equivalent. Using a serological pipette, 0.5-2.5 g of emulsion concentrate was dropped into the Nessler tube containing 47.5-49.5 water. The initial bloom was observed at zero time without stirring and the quality of the bloom was graded by visual appearance as shown below. The Nessler tube was stopped and inverted 20 times; the bloom was again recorded and so also stability as judged by volume or height of the sedimentation (cream/ppt/oil) followed at different internvals of time: 0, 1 hours, 2 hours, up to 24 hours.

Stability of Diluted Concentrate:

The composition of the cencentrate (EC) diluted with water was considered "stable" if at EC concentrtions of from 0.2 to 1%, the composition after mixing (twenty inversions) exhibited two mm or less cream and no oil in one hour. Both top and bottom should be checked.

Bloom

Excellent—Thick emulsion cloud with no separation
Good—Emulsion cloud may be thin, or may exhibit trailing, small number of oil droples within cloud
Poor—Many oil droplets within cloud, some droplets separate from cloud Each of the emulsifiable concentrates thus prepared were analyzed for ease of emulsification (bloom) upon addition of water and after twenty inversion of the sample as well as emulsion stability upon dilution with water. The composition of the samples are set forth in Table 1-2 and the results of the analysis are set forth in Table 1-3. The freeze-thaw stability was measured as follows: Compositions 1 through 7 included in Table 1-2 passed freeze-thaw stability test when stored at $-10°$ C. to 55° C. for 3 cycles of 24 hour periods. Composition 8 through 12 included in Table 1-2 passed freeze-thaw stability test when stored at 5 C. to 55° C. for 3 cycles of 24 hour periods. Formulations 11 showed maximum freeze-thaw stability with PRL at 40.7%.

TABLE 1-2

| Ingredient | 1 | 2 | 3 | 4 | 5 | 6 | 7 | 8 | 9 | 10 | 11 | 12 |
|---|---|---|---|---|---|---|---|---|---|---|---|---|
| N-methylpyrrolidone (M-Pyrol) | 30.0 | 33.0 | 0 | 30.0 | 24.0 | 60.0 | 0 | 18.2 | 22.2 | 29.7 | 20.4 | 14.8 |
| N-octylpyrrolidone (LP-100) | 30.0 | 15.0 | 0 | 0 | 18.0 | 0 | 60.0 | 7.3 | 6.7 | 3.7 | 9.3 | 11.0 |
| Aromatic oil (Exxon 200) | 0 | 12.0 | 60.0 | 30.0 | 18.0 | 0 | 0 | 11.0 | 8.2 | 3.7 | 7.4 | 11.0 |
| Gafac RE-610 | 14.3 | 14.3 | 14.3 | 14.3 | 14.3 | 14.3 | 14.3 | 21.9 | 22.2 | 22.2 | 22.0 | 22.0 |
| PRL, 92% Tech. | 25.9 | 25.9 | 25.8 | 25.8 | 25.8 | 25.8 | 25.8 | 41.6 | 40.7 | 40.7 | 40.7 | 41.2 |
| Solvent ratio | | | | | | | | | | | | |
| M-pyrol | 50 | 55 | 0 | 50 | 40 | 100 | 0 | 50 | 60 | 80 | 55 | 40 |
| LP-100 | 50 | 25 | 0 | 0 | 30 | 0 | 100 | 20 | 18 | 10 | 25 | 30 |
| Ar. Exxon 200 | 0 | 20 | 100 | 50 | 30 | 0 | 0 | 30 | 22 | 10 | 20 | 30 |
| Water used for dilution hardness ppm | WHO 342 | WHO 342 | WHO 342 | WHO 342 | WHO 342 | WHO 342 | WHO 342 | WHO 342 | WHO 342 | WHO 342 | WHO 342 | WHO 342 |
| Concentration of AAC (% in diluted sample) | 0.65 | 0.65 | 0.65 | 0.65 | 0.65 | 0.65 | 0.65 | 0.83 | 0.83 | 0.83 | 0.83 | 0.83 |

TABLE 1-3

EMULSION STABILITY AND BLOOM CHARACTERISTICS

| | Bloom | | Stability | | | |
|---|---|---|---|---|---|---|
| | Bloom at Zero Time* | After 20 Inversions** | Thickness of Separation cream, oil or precipitation at 0 time | Separation after Mixing and standing for: | | |
| | | | | 1 | 2 | 24 |
| | | | | hours | | |
| 1 | poor-fair | excellent | 20 mm cream ppt | <1 mm | <1 mm | crystals to the top |
| 2 | excellent spont. | excellent | 0 | 0 | 0 | 0 |
| 3 | excellent | excellent | 2 mm creamy | 2 mm | 2 mm | 2.5 mm |
| 4 | excellent | excellent | <1 mm | <1 mm | 1 mm | 1 mm |
| 5 | excellent | excellent | 0 | 0 | 0 | 0 |
| 6 | excellent | excellent | 0 | 0 | 0 | <1 mm |
| 7 | poor | excellent | 1 mm | <1 mm | 1 mm | 4 mm cream on bottom 4 mm oil on top |
| 8 | excellent spont. | excellent | <1 mm | trace | trace | trace |
| 9 | excellent spont. | excellent | 0 | 0 | 0 | trace |
| 10 | excellent spont. | excellent | trace | 0 | 0 | <1 mm |
| 11 | excellent spont. | excellent | trace | 0 | 0 | trace |
| 12 | excellent | excellent | <1 mm | trace | trace | trace |

TABLE 1-3-continued
EMULSION STABILITY AND BLOOM CHARACTERISTICS

| | Bloom | | Stability | | | |
|---|---|---|---|---|---|---|
| | | Thickness of Separation cream, oil or | Separation after Mixing and standing for: | | | |
| Bloom at Zero Time* | After 20 Inversions** | precipitation at 0 time | 1 | 2 | 24 | |
| | | | | hours | | |
| spont. | | | | | | |

*The descriptions have the following meanings:
poor-fair - emulsion produced between one and five minutes
excellent - emulsion produced after two seconds
spontaneous - emulsion produced instantly
**excellent - complete emulsification obtained. Thick emulsion cloud with no separation.
**good - emulsion cloud may be thin, or may exhibit trailing, small number of oil droplets within cloud
**poor - many oil droplets within cloud, some droplets separate from cloud

EXAMPLE 2

A second series of two experiments was carried out using the following formulation:

TABLE 2-1

| | | |
|---|---|---|
| 1. | CGA (98% Tech.) | 22.2% |
| 2. | N-methylpyrrolidone | 33.3% |
| 3. | N-octylpyrrolidone | 16.7% |
| 4. | Texaco Aromatic 400 | 16.7% |
| 5. | Gafac RE-610 (GAF) | 11.1% |
| | | 100.0% |

This composition was prepared by weighing out the individual quantities of the ingredients and adding the anionic emulsifier (5) to the N-methylpyrrolidone, admixing the agriculturally active chemical to this mixture, adding the N-octylpyrrolidone to the resulting mixture, and finally, adding the aromatic diluent (4) and mixing the entire composition to make it uniform. The formulatio thus prepared was clear. Samples of the formulation were stored at $-10°$ C. and $55°$ C. for each of theee 24 hr. periods. No precipitation nor separation of any of the ingredients was observed for the samples.

The concentrate thus prepared was diluted in a standard 37 cm × 2 cm Nessler's tube using WHO standard water. Two dilutions of emulsifiable concentrate to water of 5:100 and 0.6:100 were prepared. The bloom characteristics and emulsion stabilities of each of these dilutions are set forth in Table 3.

TABLE 2-2
EMULSION STABILITY AND BLOOM CHARACTERISTICS

| Formulation | I. | II. |
|---|---|---|
| Conc. of active | 22% | 22% |
| Dilution: | 2.5:47.5 (1/20) | 0.3:49.8 (1/167) |
| Water used for dilution | WHO standard 342 ppm | WHO standard 342 ppm |
| Con. of active in the diluted sample | 1.11% | 0.13% |
| Bloom at 0 time | spontaneous | spontaneous |
| After 20 inversions | excellent | excellent |
| Separation or Precipitation | | |

TABLE 2-2-continued
EMULSION STABILITY AND BLOOM CHARACTERISTICS

| Formulation | I. | II. |
|---|---|---|
| after mixing and standing for: | | |
| 1 hour | none | none |
| 2 hours | none | none |
| 4 hours | none | none |
| 10 hours | none | none |
| 24 hours | none | none |

EXAMPLE 3

A third series of expierments were carried out using the following compositions:

TABLE 3-1

| | | 3.I | 3.II |
|---|---|---|---|
| 1. | CGA (98% Tech) | 20.4% | 10.3% |
| 2. | N-methylpyrrolidone | 34.2% | 38.5% |
| 3. | N-octylpyrrolidone | 17.0% | 19.2% |
| 4. | Soybean oil (White Rose polyunsaturated vegetable oil) | 17.0% | 19.2% |
| 5. | Gafac RE-610 (GAF) | 11.4% | 12.8% |
| | | 100.0% | 100.0% |

The compositions were prepared by weighing out individual ingredients 1 through 4 and dissolving the anionic emulsifier (5) in the admixture. The entire composition was mixed in an automatic rocking shaker to obtain a uniform and clear composition. Samples of the formulations I and II were stored at $-10°$ C. and $55°$ C. for each of three 24 hour periods. No separation or precipitation of any ingredients was observed in the two samples. The concentrates thus obtained were each diluted in a standard diluents. In one case, the diluent was deionized water and in the other case, acetic acid at pH 2.5. Two dilutions of emulsifiable concentrate to diluent at 1:20 and 1:66 were prepared for each diluent. The bloom characteristics and emulsion stabilities of each of these dilutions are set forth in Table 4.

TABLE 3-2
EMULSION STABILITY AND BLOOM CHARACTERISTICS

| Formulation | I | II | III | IV | V | VI | VII | VIII |
|---|---|---|---|---|---|---|---|---|
| Emulsifiable concentrate used | 3.I | 3.I | 3.II | 3.II | 3.I | 3.I | 3.II | 3.II |
| conc. of AAC | 20.4% | 20.4% | 10.3% | 10.3% | 20.4% | 20.4% | 10.3% | 10.3% |
| water used for dilution | deionized water | deionized water | deionized water | deionized water | acetic acid | | at pH 2.5 | |
| dilution factor | 2.5/50 | 0.3/50 | 2.5/50 | 0.3/50 | 2.5/50 | 0.3/50 | 2.5/50 | 10.3/50 |

TABLE 3-2-continued

| Formulation | EMULSION STABILITY AND BLOOM CHARACTERISTICS | | | | | | | |
|---|---|---|---|---|---|---|---|---|
| | I | II | III | IV | V | VI | VII | VIII |
| conc. in the diluted sample | 1.02% | 0.12% | 1.02% | 0.12% | 1.02% | 0.12% | 1.02% | 0.12% |
| Bloom before mixing | spontaneous Excellent | spontaneous Excellent | spontaneous Excellent | spontaneous Excellent | spontaneous Excellent | spontaneous Excellent | spontaneous Excellent | spontaneous Excellent |
| after 20 inversions | Excellent | Excellent | Excellent | Excellent | Excellent | Excellent | Excellent | Excellent |
| separation after mixing and standing for: | | | | | | | | |
| 30 min. | * | * | * | * | yes, <1 mm | none | none | none |
| 1 hour | none | none | none | none | * | none | none | none |
| 2 hour | yes, 1-2 mm | none | none | none | * | none | none | 1 mm oil |
| 3 hour | * | * | * | * | * | 1 mm | 1 mm | * |
| 4 hour | yes | yes, 1-2 mm | none | none | * | * | * | * |
| 5 hour | yes | yes | yes | yes | * | * | * | * |

*Not measured.

The above expierment was preformed for evaluation of the formulation to be used as a direct feed to host animals as an insecticide. The compositions 3.I and 3.II were also diluted with soybean oil to result in 1000 ppm in AAC and did not form any ppt or separation. Thus, the formulation could be fed to the host animal (dogs) as is, or as a diluted sample in vegetable oil. e.g. soybean oil.

EXAMPLE 4

Use of N-octylpyrrolidone and N-dodecylpyrrolidone in combination.

A fourth series of experiments were carried out using the following five compositions:

TABLE 4-1

| | 4.1 | 4.2 | 4.3 | 4.4 | 4.5 |
|---|---|---|---|---|---|
| 1. N-methylpyrrolidone | 33.0% | 33.0% | 33.0% | 33.0% | 33.0% |
| 2. N-octylpyrrolidone | 0% | 10.0% | 5.0% | 7.5% | 15.0% |
| 3. N-dodecylpyrrolidone | 15.0% | 5.0% | 10.0% | 7.5% | 0% |
| 4. Aromatic petroleum oil - Exxon-200 | 12.0% | 12.0% | 12.0% | 12.0% | 12.0% |
| 5. Gafac RE-610 (GAF) | 14.2% | 14.2% | 14.2% | 14.2% | 14.2% |
| 6. PRL (same as in Example 1): 92% Tech | 25.8% | 25.8% | 25.8% | 25.8% | 25.8% |
| | 100.0% | 100.0% | 100.0% | 100.0% | 100.0% |

The compositions were prepared as explained in Example 1. Each of the emulsified concentrates thus prepared was analyzed for ease of emulsification and emulsion stability as explained under Example 1. Results are summaryized in Table 4-2. These formulations passed three cycles of freeze-thaw between −10° C. and 55° C.

TABLE 4-2

| Formulation | EMULSION STABILITY AND BLOOM CHARACTERISTICS | | | | |
|---|---|---|---|---|---|
| | I | II | III | IV | V |
| Emulsifiable concentrate used | 4.1 | 4.2 | 4.3 | 4.4 | 4.5 |
| conc. of AAC | 25.8% | 25.8% | 25.8% | 25.8% | 25.8% |
| water used for dilution | | | WHO 342 ppm hardness | | |
| dilution factor | 1.2/48.8 | 1.2/48.8 | 1.2/48.8 | 1.2/48.8 | 1.2/48.8 |
| conc. of CGA in diluted sample | 0.6% | 0.6% | 0.6% | 0.6% | 0.6% |
| Bloom before mixing | Fair | Excellent | Fair | Excellent | Excellent |
| Bloom after 20 inversions | Excellent | Excellent | Excellent | Excellent | Excellent |
| separation after mixing and standing for: | | | | | |
| 1 hour | <1 mm | 0 | Trace | 0 | Trace |
| 2 hour | 1 mm | 0 | Trace | 0 | Trace |
| 3 hour | 1 mm | 0 | <1 mm | 0 | Trace |
| 24 hour | 2 mm | 0 | 1 mm | 0 | Trace |

EXAMPLE 5

Tank Mix Compatibility

A formulation containing 16.6% of the ammomium salt of 2-[4,5-dihydro-4-methyl-4-(1-methyl ethyl)-5 OXO-1 H-imidazol-2-yl]-3 quinoline carboxylic acid, (referred to herein as SCP) in the water was prepared by dissolving an appropriate quantity of the free acid in an ammonium hydroxide solution containing a stiochiometric amount of the base. The final pH was adjusted to 7.2. It is customary to use the PRL of example 1 in conjunction with SCP in the ratio of 6:1 for better weed control. The following experiment demonstrates the compatibility of different AAC's in the composition of the invention.

Formulations 4.1, 4.2, 4.3, 4.4, and 4.5 were diluted as shown in Example 4 and summarized in Table 4-2, except that 0.5g of SCP (16.6%) was also added to the water. The effect on stability and emulsion bloom from the two AAC's present are summarized in Table 5-1.

freezed-dried SCP. The following formulation was prepared as explained in Example 1.

TABLE 6-1

| | | 6.1 | 6.2 | 6.3 | 6.4 | 6.5 |
|---|---|---|---|---|---|---|
| 1. | N-methylpyrrolidone | 35.3% | 35.3% | 35.3% | 35.3% | 35.3% |
| 2. | N-octylpyrrolidone | 16.1% | 12.0% | 8.0% | 4.0% | 0% |
| 3. | N-dodecylpyrrolidone | 0% | 4.0% | 8.0% | 12.0% | 16.0% |
| 4. | Aromatic petroleum oil - Exxon-200 | 12.8% | 12.8% | 12.8% | 12.8% | 12.8% |
| 5. | Gafac RE-610 (GAF) | 9.2% | 9.2% | 9.2% | 9.2% | 9.2% |
| 6. | PRL: 92% Tech | 23.0% | 23.0% | 23.0% | 23.0% | 23.0% |
| 7. | SCP | 3.7% | 3.7% | 3.7% | 3.7% | 3.7% |
| | (See Example 6A) | 100.0% | 100.0% | 100.0% | 100.0% | 100.0% |

The formulations shown in Example 6, i.e., 6.1 through 6.5 were diluted and the emulsion bloom and stability was evaluated as shown earlier. The results are summarized in Table 6-2. These formulations, i.e., 6.1 through 6.5, passed three cycle of freeze-thaw at 5° C. to 55° C.

TABLE 5-1

| EMULSION STABILITY AND BLOOM CHARACTERISTICS Mixed AAC's - Tank Mix Capability | | | | | |
|---|---|---|---|---|---|
| Formulation | I | II | III | IV | V |
| Emulsifiable concentrate used (Example 4) | 4.1 | 4.2 | 4.3 | 4.4 | 4.5 |
| conc. of AAC (Example 1) | 25.8% | 25.8% | 25.8% | 25.8% | 25.8% |
| water used for dilution | WHO 342 ppm hardness | | | | |
| conc. of PRL-SCP in diluted sample | 1.05% | 1.05% | 1.05% | 1.05% | 1.05% |
| conc. of PRL in diluted sample | 1.00% | 1.00% | 1.00% | 1.00% | 1.00% |
| conc. of SCP in diluted sample | 0.5% | 0.5% | 0.5% | 0.5% | 0.5% |
| Bloom at 0-time before mixing | Excellent | Excellent | Excellent | Excellent | Excellent |
| Bloom after 20 inversions | Excellent | Excellent | Excellent | Excellent | Excellent |
| separation after mixing and standing for: | | | | | |
| 1 hour | <2 mm | <2 mm | <1 mm | 1 mm | 2 mm |
| 3 hour | 2 mm | 4 mm | 1 mm | 2 mm | 4 mm |
| 18 hour | 2 mm | 4 mm | 2 mm | 2 mm | 4 mm |

Conclusion:

Use of the two component system of the invention is advantages compared to using either component along in terms of ACC stability.

EXAMPLE 6

Tank mix compatibility was also demonstrated by making the following formulations suing PRL and a

EXAMPLE 6A 16.8g of SCP 97.4% Tech. were stirred with 52 ml in ammonium hydroxide until complete solution resulted. The sample was filtered over a Whatman #4 filter under suction. The filtrate was freeze-dried at 80° C. and ≦100 milliliter vacuum for a period of 24 hours.

TABLE 6-2

| EMULSION STABILITY AND BLOOM CHARACTERISTICS | | | | | |
|---|---|---|---|---|---|
| Formulation | I | II | III | IV | V |
| Emulsifiable concentrate used | 6.1 | 6.2 | 6.3 | 6.4 | 6.5 |
| conc. of | | | | | |
| PRL | 23.0% | 23.0% | 23.0% | 23.0% | 23.0% |
| SCP | 3.7% | 3.7% | 3.7% | 3.7% | 3.7% |
| water used for dilution | WHO 342 ppm hardness | | | | |
| dilution factor | 2.5/47.5 | 2.5/47.5 | 2.5/47.5 | 2.5/47.5 | 2.5/47.5 |
| conc. of PRL in diluted sample | 1.15% | 1.15% | 1.15% | 1.15% | 1.15% |
| conc. of SCP in diluted sample | 0.185% | 0.185% | 0.185% | 0.185% | 0.185% |
| Bloom upon addition | Good | Good | Good | Fair | Excellent |
| Bloom after 20 inversions | Excellent | Excellent | Excellent | Excellent | Excellent |

TABLE 6-2-continued

| EMULSION STABILITY AND BLOOM CHARACTERISTICS | | | | | |
|---|---|---|---|---|---|
| Formulation | I | II | III | IV | V |
| separation before mixing | 4 mm | 4 mm | 4 mm | 4 mm | 2 mm |
| separation after mixing and standing for: | | | | | |
| 1 hour | 4 mm | 4 mm | 2 mm | 2 mm | 2 mm |
| 4 hour | 4 mm | 4 mm | 2 mm | 2 mm | 3 mm |
| 18 hour | 4 mm | 4 mm | 2 mm | 2 mm | 3 mm |

Formulations 6.3 and 6.4 produced improved stability on dilution. The cream re-emulsified after 10 inversions and reappeared 15 minutes after the 10 inversions.

EXAMPLE 7

The following formulations 7.1 through 7.5 were prepared exactly as explained in Example 1, except that $N^3$, $N^3$, di-N-propyl-2,3-dinitro-6-trifuloromethyl-M-phenylenediamine (PRO) was used. These formulations passed three cycles of freeze-thaw at 5° C. to 55° C.

TABLE 7-1

|  |  | 7.1 | 7.2 | 7.3 | 7.4 | 7.5 |
|---|---|---|---|---|---|---|
| 1. | N-methylpyrrolidone | 34.7% | 34.7% | 34.7% | 34.7% | 34.7% |
| 2. | N-octylpyrrolidone | 15.8% | 11.8% | 7.9% | 4.0% | 0% |
| 3. | N-dodecylpyrrolidone | 0% | 4.0% | 7.9% | 11.8% | 15.8% |
| 4. | Aromatic petroleum oil - Exxon-200 | 12.6% | 12.6% | 12.6% | 12.6% | 12.6% |
| 5. | Gafac RE-610 (GAF) | 10.6% | 10.6% | 10.6% | 10.6% | 10.6% |
| 6. | PRO: 94.7% Tech | 26.3% | 26.3% | 26.3% | 26.3% | 26.3% |
|  |  | 100.0% | 100.0% | 100.0% | 100.0% | 100.0% |

The above formulations were diluted and the emulsion characteristics were evaluated as before. The results are summarized in Table 8. The results show that the use of dodecylpyrrolidone or a mixture of 75:25 N-dodecylpyrrolidone and N-octylpyrrolidone used as the second component resulted in better emulsion stability when compared to use of N-octylpyrrolidone alone.

TABLE 7-2

| EMULSION STABILITY AND BLOOM CHARACTERISTICS | | | | | |
|---|---|---|---|---|---|
| Formulation | I | II | III | IV | V |
| Emulsifiable concentrate used | 7.1 | 7.2 | 7.3 | 7.4 | 7.5 |
| conc. of PRO | 26.3% | 26.3% | 26.3% | 26.3% | 26.3% |
| water used for dilution | | | WHO 342 ppm hardness | | |
| dilution factor | 2.5/47.5 | 2.5/47.5 | 2.5/47.5 | 2.5/47.5 | 2.5/47.5 |
| conc. of PRO in diluted sample | 1.31% | 1.31% | 1.31% | 1.31% | 1.31% |
| Bloom at 0-time before mixing | Excellent | Excellent | Excellent | Excellent | Excellent |
| Bloom after 20 inversions | Excellent | Excellent | Excellent | Excellent | Excellent |
| separation before mixing | 1 mm | 1 mm | Trace | 0 | 0 |
| separation after mixing and standing for: | | | | | |
| 0 hour | 2 mm | 2 mm | 0 | 0 | 0 |
| 1 hour | 2 mm | 2 mm | <1 mm | Trace | Trace |
| 2 hour | 3 mm | 3 mm | 1.5 mm | 1 mm | 1 mm |
| 3 hour | 3 mm | 3 mm | 1.5 mm | 1 mm | 1 mm |
| 4 hour | 4 mm | 4 mm | 2 mm | 1 mm | 1 mm |

EXAMPLE 8

The following formulations 8.1 through 8.16 were prepared exactly as explained in Example 1 except that a fungicide N,N'-(1,4-piperazinediyl bis (2,2,2-trichloro) ethylidend)bisforamide (TRI) was used.

TABLE 8-1

|  |  | 8.1 | 8.2 | 8.3 | 8.4 | 8.5 | 8.6 | 8.7 | 8.8 |
|---|---|---|---|---|---|---|---|---|---|
| 1. | N-methylpyrrolidone | 42.6% | 42.6% | 42.6% | 42.6% | 42.6% | 42.6% | 42.6% | 44.0% |
| 2. | N-octylpyrrolidone | 19.4% | 19.4% | 9.7% | 9.7% | — | — | — | 10.0% |
| 3. | N-dodecylpyrrolidone | — | — | 9.7% | 9.7% | 19.4% | 19.4% | 19.4% | 10.0% |
| 4. | Aromatic petroleum oil - Exxon-200 | 15.5% | 15.5% | 15.5% | 15.5% | 15.5% | 15.5% | 15.5% | 16.0% |
| 5. | Gafac RE-610 | 6.4% | — | 6.4% | — | 6.4% | — | — | 10.0% |
| 6. | Gafac RM-710 | — | 6.4% | — | 6.4% | — | 6.4% | — | — |
| 7. | TRI | 16.1% | 16.1% | 16.1% | 16.1% | 16.1% | 16.1% | 16.1% | 10.0% |
| 8. | Dodecyl benzene sulfonic acid Tech: 97% | — | — | — | — | — | — | 6.4% | — |
| 9. | Aromatic petroleum | — | — | — | — | — | — | — | — |

TABLE 8-1-continued

| | | 8.1 | 8.2 | 8.3 | 8.4 | 8.5 | 8.6 | 8.7 | 8.8 |
|---|---|---|---|---|---|---|---|---|---|
| | oil - Texaco-150 | | | | | | | | |
| 10. | Iso octylpyrrolidone (N-2'ethyl hexyl-pyrrolidone) | — | — | — | — | — | — | — | 6.4% |
| | | 100.0% | 100.0% | 100.0% | 100.0% | 100.0% | 100.0% | 100.0% | 100.0% |

| | | 8.9 | 8.10 | 8.11 | 8.12 | 8.13 | 8.14 | 8.15 | 8.16 |
|---|---|---|---|---|---|---|---|---|---|
| 1. | N-methylpyrrolidone | 15.0% | 24.0% | 24.0% | 24.0% | 32.0% | 32.0% | 32.0% | 24.0% |
| 2. | N-octylpyrrolidone | 40.0% | 32.0% | 16.0% | — | 32.0% | 16.0% | — | — |
| 3. | N-dodecylpyrrolidone | — | — | 16.0% | 32.0% | — | 16.0% | 32.0% | — |
| 4. | Aromatic petroleum oil - Exxon-200 | — | 24.0% | 24.0% | 24.0% | 16.0% | 16.0% | 16.0% | 24.0% |
| 5. | Gafac RE-610 | — | 8.0% | 8.0% | 8.0% | 8.0% | 8.0% | 8.0% | 8.0% |
| 6. | Gafac RM-710 | 5.0% | — | — | — | — | — | — | — |
| 7. | TRI | 7.5% | 12.0% | 12.0% | 12.0% | 12.0% | 12.0% | 12.0% | 12.0% |
| 8. | Dodecyl benzene sulfonic acid Tech: 97% | — | — | — | — | — | — | — | — |
| 9. | Aromatic petroleum oil - Texaco-150 | 32.5% | — | — | — | — | — | — | — |
| 10. | Iso octylpyrrolidone (N-2'ethyl hexyl-pyrrolidone) | — | — | — | — | — | — | — | 32.0% |
| | | 100.0% | 100.0% | 100.0% | 100.0% | 100.0% | 100.0% | 100.0% | 100.0% |

The ease of emulsification and emulsion stability of the above six formulations were evaluated after dilution, as before, and the results are summarized in Table 8-2.

TABLE 8-2

EMULSION STABILITY AND BLOOM CHARACTERISTICS

| Formulation | I | II | III | IV | V | VI | VII |
|---|---|---|---|---|---|---|---|
| Emulsifiable concentrate used | 8.1 | 8.2 | 8.3 | 8.4 | 8.5 | 8.6 | 8.7 |
| conc. of TRI | 16.1% | 16.1% | 16.1% | 16.1% | 16.1% | 16.1% | 16.1% |
| water used for dilution | | | | WHO 342 ppm hardness | | | |
| dilution factor | 2.45/47.5 | 2.45/47.5 | 2.45/47.5 | 2.45/47.5 | 2.45/47.5 | 2.45/47.5 | 2.45/47.5 |
| conc. of TRI in the diluted sample | 0.81% | 0.81% | 0.81% | 0.81% | 0.81% | 0.81% | 0.81% |
| Bloom before mixing | Fair-Good | Fair | Fair-Good | Fair | Fair-Good | Fair-Good | Poor |
| after 20 inversions | Excellent | Excellent | Excellent | Excellent | Excellent | Excellent | Excellent |
| separation at 0 time | 4 mm | 5 mm | 3 mm | 5 mm | 3.5 mm | — | 8 mm |
| ppt/separations after mixing and standing for: | | | | | | | |
| 0 hour | 0 | 0 | 0 | 0 | 0 | 0 | 0 |
| 1 hour | 2 mm | 2 mm | 2 mm | 4 mm | 2 mm | 2 mm | 4 mm, oil |
| 2 hour | 2 mm | 2 mm | 2 mm | 4 mm | 2 mm | 3 mm | 4 mm, oil |
| 4 hour | 4 mm | 4 mm | 3.5 mm | 5 mm | 3.5 mm | 3.5 mm | |

| Formulation | VIII | IX | X | XI | XII | XIII | XIV | XV | XVI |
|---|---|---|---|---|---|---|---|---|---|
| Emulsifiable concentrate used | 8.8 | 8.9 | 8.10 | 8.11 | 8.12 | 8.13 | 8.14 | 8.15 | 8.16 |
| conc. of TRI | 10% | 7.5% | 12% | 12% | 12% | 12% | 12% | 12% | 12% |
| water used for dilution | | | | | WHO 342 ppm hardness | | | | |
| dilution factor | 0.8/49.2 | 1.0/49 | 0.7/49.3 | 0.7/49.3 | 0.7/49.3 | 0.7/49.3 | 0.7/49.3 | 0.7/49.3 | 0.7/49.3 |
| conc. of TRI in the diluted sample | 0.16% | 0.15% | 0.17% | 0.17% | 0.17% | 0.17% | 0.17% | 0.17% | 0.17% |
| Bloom before mixing | Poor | Poor | Fair | Good | Fair | Fair | Fair | Fair | Fair |
| after 20 inversions | | | | | Excellent | | | | |
| ppt/separations after mixing and standing for: | | | | | | | | | |
| 1 hour | — | — | Trace | Trace | 0 | Trace | Trace | Trace | Trace |
| 2 hour | Trace | 0 | — | — | — | — | — | — | — |
| 4 hour | <1 mm | 0 | Trace | Trace | Trace | <1 mm | <1 mm | Trace | <1 mm |
| 24 hour | 1 mm | 1 mm oil on top | 1.5 mm | 1 mm | <1 mm | 1.5 mm | 1 mm | 1 mm | <1 mm |
| *after 24 hour settling, filtered through screens | | | | | | | | | |
| 60 mesh | + | — | — | + + | + + | + | — | — | ± |
| 100 mesh | + | — | + | ± | ± | + | ± | — | ± |
| 250 mesh | + ± | — | ± | + + | + + | + ± | ± ± | ± | ± ± |

\* — means no sediment;
± means trace;
± ± means more than trace sediment but unmeasurable by weighing.

EXAMPLE 9

The following formulation 9.1 was prepared exactly as explained in Example 1, except that N-(2'-ethylhexylpyrrolidone) was used in the place of N-octylpyrrolidone.

TABLE 9-1

| Formulation and % Composition | | |
|---|---|---|
| | | 9.1 |
| 1. | N-methylpyrrolidone | 33.0% |
| 2. | N-(2'-ethylhexylpyrrolidone) | 15.0% |
| 3. | Aromatic Petroleum oil - Exxon 200 | 12.0% |
| 4. | PRL Tech. 92% (see Example 1) | 26.0% |
| 5. | Gafac RE-610 (GAF) | 14.0% |
| | TOTAL | 100.0% |

This formulation did not freeze at 5° C. The ease of emulsificiation and stability on dilution are shown in Table 9-2.

TABLE 9-2

| Formulation | 9.1 |
|---|---|
| Conc. of PRL: | 26.0% |
| Water used for dilution | WHO 342 PPM hardness |
| Dilution factor | 2.5 g/47.5 g |
| Conc. of PRL in the diluted sample | 1.3% |
| Bloom at 0 time | Excellent |
| Bloom after 20 inversions | Excellent |
| Separation of cream after 20 inversions and on standing after: | |
| 1 hour | Trace |
| 3 hours | <1 mm |
| 4 hours | <1 mm |

TABLE 9-2-continued

| Formulation | 9.1 |
|---|---|
| 24 hours | <1 mm |

After standing for 24 hours, 20 inversions and filtration through 60 mesh, 100 mesh and 2590 mesh screens, no sediment was left, even on a 250 mesh screen.

What is claimed is:

1. A stable emulsifiable concentrate comprising an agriculturally active herbicide which is substantially insoluble in water, an organic diluent, a surfactant and a solvent composed of first and second components, said first component having a sufficiently high hydrophilic property and being present in an amount effective to solubilize the agriculturally active herbicide, and the second component being selected from the group consisting of octylpyrrolidone, dodecylpyrrolidone, N-2-ethylhexylpyrrolidone, and mixtures thereof, and being present in an amount, in conjunction with a surfactant, effective to disperse the agriculturally active herbicide.

2. A stable emulsifiable concentrate comprising an agriculturally active herbicide which is substantially insoluble in water, an aromtic petroleum oil comprising about 60% of heavy aromatic solvent naptha and about 40% of middle distillate solvent extractant having a fractional dispersive solubility parameter of greater than about 70% and a molar volume of greater than about 90 $CM^3$/mole, a surfactant and a solvent composed of first and second components, said first component having a sufficiently high hydrophilic property and being resent in an amount effective to solubilize the agriculturally active herbicide, and the second component being selected from the group consisting of octylpyrrolidone, dodecylpyrrolidone, N-2-ethylehxypyrrolidone, and mixtures thereof, and being present in an amount, in conjunction with a surfactant, effective to disperse the agriculturally active herbicide.

* * * * *